United States Patent [19]

Eigler et al.

[11] Patent Number: 5,077,210

[45] Date of Patent: Dec. 31, 1991

[54] IMMOBILIZATION OF ACTIVE AGENTS ON SUBSTRATES WITH A SILANE AND HETEROBIFUNCTIONAL CROSSLINKING AGENT

[76] Inventors: Frances S. Eigler, 12400 Beall Mt. Rd., Potomac, Md. 20834; Jacque Georger, 8409 Great Lake La., Springfield, Va. 22152; Suresh K. Bhatia, 4801 Kanmore Ave., Alexandria, Va. 22304; Jeff Calvert, 6033 Wimington Dr., Burke, Va. 22015; Lisa C. Shriver-Lake, 6073 Hollow Knoll Ct., Springfield, Va. 22152; Reinhard Bredehorst, 4101 W. St. NW., Washington, D.C. 20007

[21] Appl. No.: 297,088

[22] Filed: Jan. 13, 1989

[51] Int. Cl.$^5$ .............. C12N 11/14; C12N 11/04; G01N 33/551; G01N 33/549

[52] U.S. Cl. .................. 435/176; 435/181; 436/524; 436/527; 436/532; 530/811; 530/816

[58] Field of Search ............ 435/176, 181; 436/524, 436/527, 532; 530/811, 816

[56] References Cited

U.S. PATENT DOCUMENTS

| | | | |
|---|---|---|---|
| 3,669,841 | 6/1972 | Miller | 435/176 |
| 4,176,006 | 11/1979 | Cormier et al. | 435/176 X |
| 4,517,303 | 5/1985 | Freytag et al. | 436/501 |
| 4,894,229 | 1/1990 | Polson et al. | 435/176 X |

OTHER PUBLICATIONS

Weetall, H. H., Methods in Enzymology, vol. 44, 1976, Academic Press, N.Y., pp. 134-149.

Jonsson et al., Method in Enzymology, vol. 137, 1988, Academic Press, N.Y., pp. 381-394.

*Primary Examiner*—David M. Naff
*Attorney, Agent, or Firm*—Wolf, Greenfield & Sacks

[57] ABSTRACT

Active agents such as proteins are covalently immobilized on substrates carrying hydroxyl groups. A silane is bound to the substrate and coupled to a heterobifunctional crosslinker at one functional group leaving a free functional group, different than the first group, to which a protein is bound while retaining high protein functionality. Preferably, the silane has a functional group which reacts with the hydroxyl group of the substrate and a thiol terminal group which reacts with a functional group of a heterobifunctional crosslinking agent which contains a succinimide group that reacts with an amino group of the active agent. Bound active agents such as proteins are useful as biosensors or reactants in a variety of applications including bioassays.

27 Claims, 3 Drawing Sheets

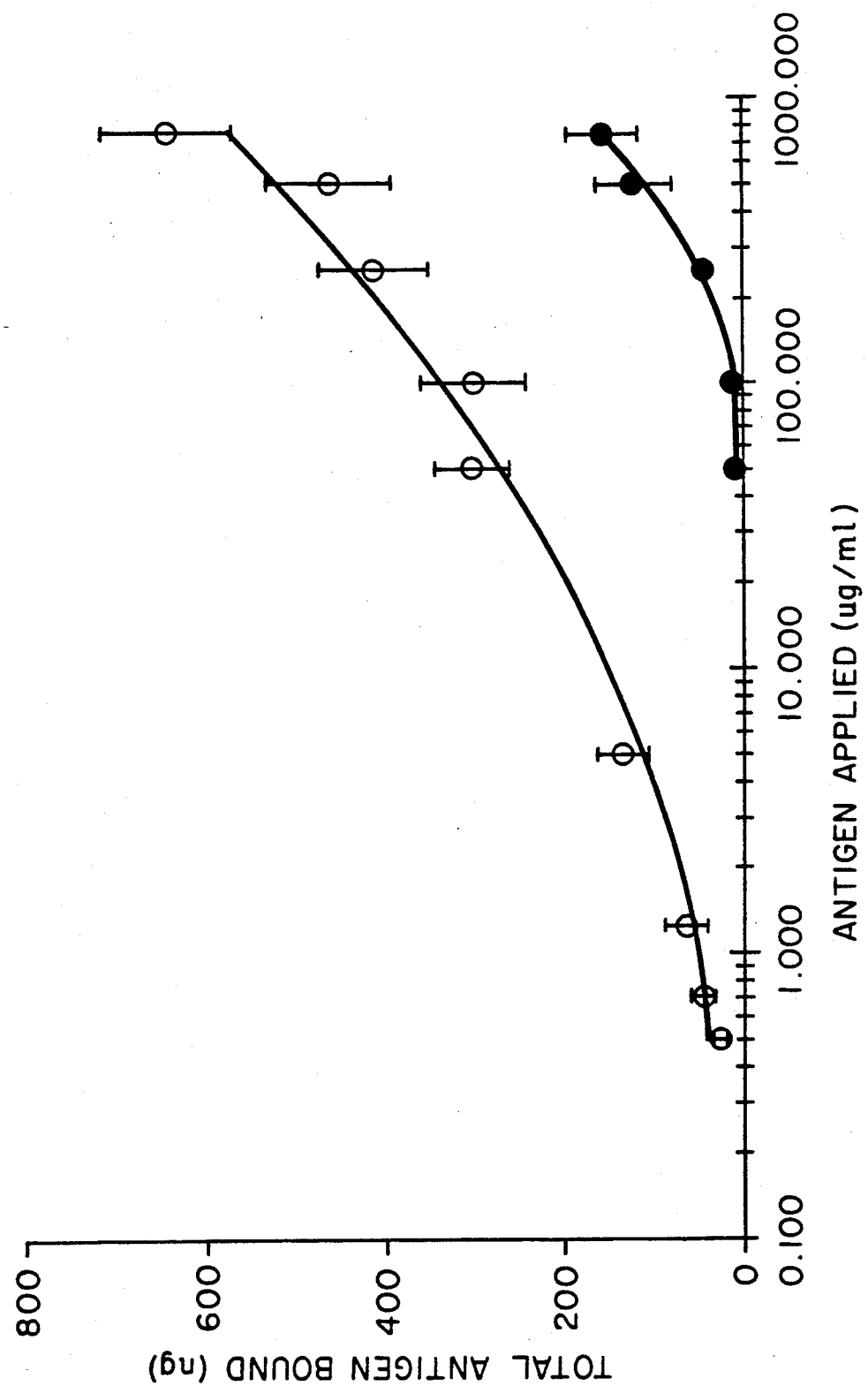

IMMOBILIZATION OF ACTIVE AGENTS ON SUBSTRATES WITH A SILANE AND HETEROBIFUNCTIONAL CROSSLINKING AGENT

BACKGROUND OF THE INVENTION

Active agents which are preferably functional organic materials such as proteins, have been immobilized in the past on a wide variety of solid supports for various known applications including analysis, separation, synthesis and detection of biological and other materials. Often hydrophilic polymers have been used to immobilize the proteins because it is less difficult to attach proteins to polymers than to inorganic materials. However, there is an increasing need to immobilize functional organic material such as proteins on inorganic material such as silica, glass, silicon, metals and the like. Problems can arise with nonspecific protein adsorption to inorganic material.

Proteins such as antibodies can be attached to quartz or glass by simple adsorption, however, often such immobilized proteins can partially de nature and tend to leech or wash off the surface. Van der Merwe (U.S. Pat. No. 4,478,946) suggests the adsorption of nonfunctional proteins to a surface and the employment of crosslinking agents to covalently attach the functional proteins to the adsorbed nonfunctional proteins. However, the adsorption approach gives less than desirable attachment.

The prior art has suggested modifying surface hydroxyl groups of inorganic substrates to provide functionality that reacts directly with proteins (see U.S Pat. No. 4,415,665, U.S. Pat. No. 4,582,875 and U.S. Pat. No. 4,562,157). European patent No. 87,401,000.

Various methods for coating inorganic substrates with silane films have been reviewed, Weetal H. H. (1976) Methods in Enzymology, Volume 44, 134-148, Academic Press, New York, NY. Inorganic porous substrates coated with epoxy silane have been oxidized to produce aldyhyde groups reacting directly with antibodies, Sportsman, J. R. et al (1980) Anal. Chem. 52,2013-2018. Others, such as Sagiv U.S. Pat. No. 4,539,061, have established multilayers of silanes deposited on silica. Proteins have further been linked to silane films on silica using glutaraldehyde. See U.S. Pat. No. 4,478,946, Mandenius, C.F., et al (1984) Anal. Biochem. 137, 106-114, and Richards, F. M. et al (1968) J. Mol. Biol. 37, 231-233. Reactive crosslinkers such as glutaraldehyde may bind to many residues and form multi protein complexes which could interfere with protein function. To avoid the use of glutaraldehyde, others have modified silica surfaces with epoxy silanes and subsequently altered the silanes to have a dihydroxy terminus, U.S. Pat. No. 4,562,157. This method involved many steps and can have problems with the density of protein adsorbed to epoxy silane film. More recently, Jonsson, U. et al, Volume 137, 381-394 Methods in Enzymoloqy (1988) has suggested the use of silane films on specific inorganic surfaces and specific crosslinking agents which can be heterobifunctional, but in all cases, appear to require a free sulfhydryl group on the protein to be bound. This requires that nearly all proteins be modified prior to immobilization. Thus either a free-SH must be attached (a chemical modification which must be carefully controlled in order to avoid damage to the protein) or existing S-S bonds must be reduced. In the case of attaching antibodies to an amino terminal silane, this approach involves proteolysis and reduction to produce Fab fragments from intact antibodies. Such fragments can have reduced binding affinity for antigen and significant amounts can be lost during processing.

BRIEF DESCRIPTION OF THE INVENTION

It is an object of this invention to provide a method for immobilizing a high density of functional organic materials such as proteins on a substrate under conditions which maintain the functionality of the materials.

Another object of this invention is to provide a method useful in adhering an active agent to a hydroxyl carrying surface which method includes binding a silane to the surface and using a heterobifunctional crosslinking agent having one functional group reactive with a free functional group of the silane and having a second functional group which is nonreactive with the free functional group of the silane so that the second functional group is free to act as an available site for binding the active agent such as proteins.

Still another object of the invention is to provide a method in accordance with the preceding method wherein the active agent is bound to the available site and the resultant product has strong covalent bonds maintaining the active agent in position.

Still another object is to provide products produced in accordance with the preceding objects which are useful as biosensors, adsorbants and materials for a variety of biological and analytical uses.

It is a further object of this invention to provide products in accordance with the preceding object where stable covalent bonding of an active agent to an inorganic substrate is achieved, a high density of active agent can be obtained on a support surface, if desired, and the active agent can retain a high level of activity after bonding.

According to the invention, a method for modifying a substrate to activate said substrate for the immobilization of active agents is provided. The method comprises selecting a substrate having hydroxyl groups on at least one surface. The surface is then coated with a silane containing at least two reactive sites wherein at least one of the reactive sites is capable of reacting only with the hydroxyl groups on the surface and at least one of the reactive sites is nonreactive with the hydroxyl on the surface, to form a silane film having an available reactive group. The silane layer formed is coated with a heterobifunctional crosslinking agent wherein one of the functional groups is reactive only with the available reactive group on the silane and the other of the functional groups is nonreactive with the available group on the silane to form a layer of crosslinking agents having an available reactive site. The active agent is actually immobilized on the substrate by then coating the crosslinking agent layer with an active agent having at least one site capable of being bound by the available site on the crosslinking agent.

According to the invention a product for supporting an active agent comprises a substrate having a layer of silane molecules having two active ends and linked to the substrate at only one reactive end by reaction with a hydroxyl group. A layer of a heterobifunctional crosslinking agent, having two reactive sites and linked to the silane at only one end is provided, with a reactive site of the crosslinking agent being available at the other end for attachment of active agents. In the preferred product the active agent forms a layer bound by the other end of the crosslinking agent. More preferably, the active agent is bound without modifying the active agent prior to reaction with the crosslinking agent and the active agent has high functionality in the final product.

According to the invention, a method of immobilizing active agents such as functional materials which can be organic or inorganic and are selected from a class consisting of antibodies, antigens, enzymes nucleic acid probes, receptors, chelators, ionophores, lipids, mammalian plant and other biological cells, other proteins, and combinations of the above are used. A substrate having hydroxyl groups on a surface thereof is selected. In the preferred embodiment the substrate is an inorganic substrate which can be for example, glass, quartz, silicon, metal or the like. A silane film is deposited thereon to covalently bind with the hydroxyl groups of the substrate leaving a free reactive group on a surface of the silane. Preferably the silane is a thiol terminal silane. A heterobifunctional crosslinking agent having first and second functional groups is reacted with the free reactive group of the silane so that the first functional group of the crosslinking agent binds with the silane leaving a second functional group free and preferably capable of reacting with an unmodified form of the organic material.

The second functional group of the crosslinking agent is reacted with the active agent to form a strong covalent bond, with the organic material having a high degree of functionality after forminq the covalent bond. At least one blocking agent may be added to prevent nonspecific action between the surface of the substrate, the silane film, the crosslinker, or the active agent and undesirable components of whatever environment. Blocking agents such as detergents, proteins and the like can be used as known in the art.

In some cases the product can be provided with the substrate, silane film and bound crosslinker. A second related product can be formed by binding an active agent to the crosslinker.

The resultant highly useful products of this invention have a bound active agent, such as a protein, at high density covalently bound on the substrate with the protein maintaining high functionality.

It is a feature of this invention that a high density of active agents, such as antibodies, antigens, enzymes, receptors, or the like, can be coupled by strong bonds to a variety of hydroxyl-carrying surfaces under conditions which minimize damage to the proteins. The substrates can be optical fibers, silicon or glass surfaces. Where antigens or antibodies are immobilized on such substrate products of this invention can be used in adaptions of common immunoassay procedures to enable measurements of antigen or antibody. It is a feature of this invention that a crosslinking agent is positioned between the silane and the protein to covalently link the terminal group of the silane with a specific group of the protein. The consequent linkage provides a high density of proteins attached to the surface in a reproducible manner while maintaining the function of the protein. In the preferred embodiments the proteins can be unmodified when reacted with the crosslinking agent.

BRIEF DESCRIPTION OF THE DRAWINGS

The above and other features, objects and advantages of the present invention will be better understood from a reading of the following specification in conjunction with the enclosed drawings in which:

FIG. 3 illustrates a sensitivity study for the amount of antigen bound. Cover slips coated with MDS, GMBS, and either (goat IqG) (control antibody) or rabbit anti-goat IqG (specific antibody) were incubated with iodinated antigen (goat IgG) at concentrations ranging from 0.5 ug/ml to 750 uq/ml in PBS containing 2 mg/ml BSA. After one hour the cover slips were washed and radioactivity measured. The amount of antigen bound by the immobilized antibody was proportional to the amount of antigen in solution between 0.5 and 100 ug/ml.

DESCRIPTION OF PREFERRED EMBODIMENTS

Figure 1:
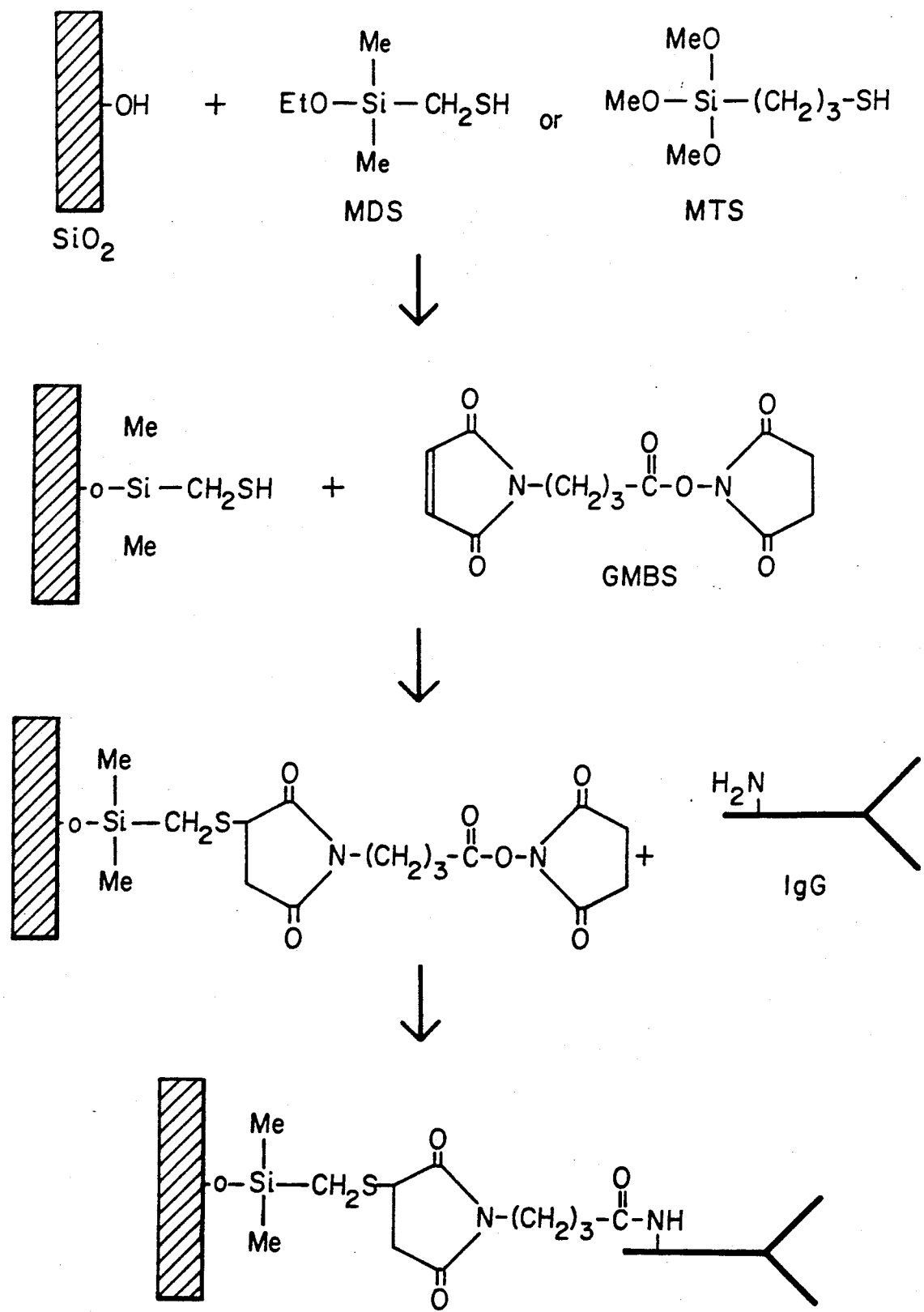
FIG. 1 shows an example of an immobilization procedure for covalent attachment of proteins to a silica surface.

As best shown in FIG. 1, a substrate in accordance with this invention, such as silicon dioxide, having free hyroxyl groups is reacted with a silane such as MDS or MTS to form the silane film which is then reacted with a heterobifunctional crosslinker to bind the crosslinker to the thiol functional end of the silane film. This leaves an available functional group which can be reacted with IgG to form the final bound protein on the silica surface shown in FIG. 1.

Thus there is essentially a four step process which comprises a) selection of a substrate having hydroxyl groups, b) forming a silane film which covalently bonds the hydroxyl groups leaving a free functional end, c) reacting the free functional end of the silane with one functional end of a heterobifunctional crosslinker leaving a free end of a crosslinker which is preferably capable of reacting with an organic material, such as an unmodified protein, and d) attaching the protein or other active agent. Blocking agents can be used. These agents can be proteins, polymers, amphiphiles, detergents or carbohydrates and can be added to the reaction at the appropriate time after attachment of the silane film to avoid non-specific protein attachment and reaction or interference with later applications.

The substrates which can be used in the method and product of the present invention include substrates which have or can be modified to have functional groups such as hydroxyl groups which can be reacted with silanes. Suitable substrates are preferably inorganic substrates including but not limited to silicon, glass, silica, quartz, metal oxides and the like which can be for example optical fibers, wires, wafers, discs or planar surfaces, microscope slides, or beads, as well as organic polymers Organic polymers useful as substrates include polvinyl alcohol polymers, acrylic acid polymers and others. Generally the substrates have or can be modified to have functional groups such as surface hydroxyl groups that react with silanizinq reagents.

The silanes useful to bind to the hydroxyl groups in a covalent bond can be a variety of silanes. Thiol-terminated silanes are preferred for attachment sites although films can include those with a epoxy, amino, olefin or carboxyl terminus. The Si end of the molecule can be trimethoxy, cholor or monomethoxy. Typical silanes useful in the present invention include thiol-terminated silanes such as mercaptomethyldimethylethoxysilane (MDS) and 3 mercaptopropyltrimethoxysilane (MTS). Other silanes include ADS, ATS and GTS as described with reference to Table I. Generally the useful silanes bind only to one of the two reactive groups on the heterobifunctional crosslinker.

The crosslinking agents having first and second functional groups are heterobifunctional crosslinking agents having different reactive groups at each end. Reactive groups include amino reactive functionalities such as n-hydroxysuccinimide active esters, imidoesters and nitroaryl halides or thiol-reactive functions such as pyridyl disulfides, maleimides, and active haloqens. Four heterobifunctional agents found particularly useful to couple antibodies to a thiol terminal silane film are listed below with each having a succinimide group on one end to bind the protein, but with a variable other end;

N-qamma-maleimidobutyryloxy succinimide ester (GMBS) has a maleimide terminal group.

N succinimidyl 3 (2-pyridyldithio) propionate (SPDP) has a protected thiol

N succinimidyl (4 iodoacetyl) amino benzoate (SIAB) has an active halogen, succinimidyl 4-(p-maleimidophenyl) butyrate (SMPB) has maleimide adjacent to a phenyl ring.

The active agents such as functional organic materials to be immobilized can be a wide variety of biological materials including proteins, such as antibodies, antigens, enzymes, nucleic acid probes, lectins, receptors, chelators, ionophores, lipids, channel forming proteins, mammalian, plant and other biological cells. Materials including those often used for immunoassay such as antigens and antibodies, enzymes, receptors, haptens, hormones and the like can be used. Nucleic acid probes and other DNA portions can be bound.

A desired activity of the active agent used is maintained after immobilization on the surface. For example, receptors retain ability to bind ligands, antibodies maintain ability to bind antigen and vice versa, enzymes maintain ability to carry out catalytic action, nucleic acid probes still form duplexes with complimentary nucleic acid strands. Similarly lectins bind appropriate substrates, ionophores maintain ability to bind appropriate ions. Lipids can be bound without loosing ability to form films or other microstructures on the surface and channel forminq proteins can be bound without loosing ability to open closed channels.

Blocking agents may be used to maintain specific bindings as required. Blocking agents include detergents such as Triton X 100 and Tween. Other blocking agents including BSA, ovalbumin, glucose, other sugars, polyethylene glycol, dextran, lysozyme, and poly L-lysine may also be used in some embodiments.

After attachment of the protein further blocking agents can be used in further procedures to assure interaction of the protein with a desired material.

The process and products of this invention can be used in many areas of the art. For example, immumunoassay with immobilized antigen or antibody is well known in the art. Similarly coatings for waveguides and optical fibers with antigens or antibodies can be formed.

In one use where bound protein is antibody, antigen can be radiolabeled with $^{125}I$ or fluorescent dye and passed over an immobilized antibody in accordance with this invention to determine the amount of bound antigen in accordance with known procedures.

The specific conditions for each of the reactions of the present invention, to obtain covalent bonding at the substrate between the silane and the substrate, between the crosslinker and the silane film, and between the protein and the crosslinker can vary greatly depending upon the specific materials used. In all cases, the reaction between the crosslinker and the protein is nondestructive to the silane film. The crosslinker has high affinity for the proteins or other active agents where desired the active agents can be deposited at high densities, which densities can vary greatly depending on the specific materials used.

In a preferred usage, covalent immobilization of functional proteins on silica substrates uses a thiol-terminal silane and heterobifunctional crosslinkers to bind a high density of functional protein to planar surfaces and fibers such as silica fibers. It has been found that antibodies can be immobilized in the range of, for example. 0.66 ng/mm$^2$ to 0.9 ng/mm$^2$ using radiolabeled antibody. The relative amount of IqG antigen bound by the immobilized antibody (0.37 to 0.55 mole antigen/mole antibody) can be 3 to 5 times greater than other investigator have reported. In addition, the amount of protein nonspecifically adsorbed to the antibody coated surface can be further reduced by the addition of blocking agents so that nonspecific adsorption of protein antigens represents only 2–6% of the total antigen binding. With this low background, antigen binding could be measured at levels as low as 150 femtomoles when an antigen concentration of 3 picomoles/ml is applied. The process for antibody immobilization is straight forward, easy to perform, and adaptable for modifying mass quantities of biosensor components.

In a specific example of carrying out a preferred embodiment of this invention, the following steps were used with substitution of crosslinkers as noted.

Coverslips (1.1 cm×4.4 cm, made of #2 glass) and optical fibers (550 micron diameter fused silica) were used. The fibers were cut into 4.4 cm long pieces and immersed in concentrated nitric acid for 30 min followed by several washings with distilled water before use. 4 Aminobutyldimethylmethoxysilane (ADS), 4-aminobutyltriethoxysilane (ATS), and mercaptomethyldimethylethoxysilane (MDS) were purchased from Petrarch Systems, Bristol, PA 3-Mercaptopropyltrimethoxysilane (MTS) and 3-qlycidoxypropyltrimethoxsilane (GTS) were obtained from Fluka, Hauppauqe, NY and Aldrich, Milwaukee, WI respectively. The heterobifunctional crosslinkers N gamma-maleimidobutyryloxy succinimide ester (GMBS) (Calbiochem, San Diego, CA), N-succinimidyl-3-(2-pyridyldithio) propionate (SPDP) (Pierce, Rockford, IL), N-succinimidyl-(4-iodoacetyl) aminobenzoate (SIAB) (Pierce) and succinimidyl 4-(p-maleimidophenyl) butyrate (SMPB) (Pierce) were constantly stored at 4$^{0}$C. Toluene was kept over type 3 A molecular sieves. The silane films were analyzed by contact angle using a NRL Zisman-type contact angle goniometer. Bovine serum albumin (BSA) was purchased from Siqma, St. Louis, MO. Affinity purified rabbit anti-goat IqG, goat IqG, and mouse IgG (Jackson Immunoreserach, West Grove, PA) and sheep anti-mouse IgG (Cooper Diagnostics, Inc. West Chester, PA) were kept in the refrigerator and diluted to the required concentration with phosphate buffered saline (PBS, pH 7.4) just prior to use. $^{125}$-I labelled proteins were prepared using Iodo-beads (Patrella, E. et al (1887) J. Immun. Meth. 104,159) and radioactively was measured on a Packard scintillation counter. NMR spectra were recorded on a Bruker MSL 300 instrument fitted with an Aspect 3000 computer and a high resolution 5 mm l' H probe. The spectra were taken in CDCl$_3$ with (CH$_3$)$_4$ Si as an internal standard.

Cleaning of Silica Surfaces and Silanization

Two substrates, glass cover slips and fused silica optical fibers, were used. The substrates were acid cleaned by immersion in a 1:1 mixture of concentrated hydrochloric acid and methanol for 30 minutes followed by rinsing several times with doubly distilled water. Next, the substrates were treated with concentrated sulfuric acid for 30 minutes, rinsed several times with distilled water, and boiled for 30 minutes in distilled water to produce a maximum number of free hydroxyl groups. Finally, the substrates were drained onto a piece of low lint tissue and allowed to air dry.

In a glove bag under an inert atmosphere, the cover slip or fiber was placed in a 2% solution of mercaptomethyldimethylethoyxsilane (MDS) or mercaptopropyltrimethoxysilane (MTS) in dry toluene for a period of 2 h. The substrate was removed from the solution, rinsed in dry toluene and allowed to air dry. A similar technique was used for making films with other silanes.

Treatment of Silanized substrate with a heterobifunctional crosslinker

The organic crosslinking reagent was dissolved in a minimum amount of dimethylformamide (DMF) and diluted with absolute ethanol to a final concentration of 2 mM. The silanized substrate was treated with crosslinker for 1 h and washed in PBS. The crosslinker, GMBS was used except where otherwise specified.

Immobilization of the Antibody

A 0.05 mq/ml solution IqG antibody (affinity purified rabbit anti-goat IgG) or control antibody (goat IgG, mouse IgG or sheep anti-mouse IgG) in PBS was placed on the substrate coated with silane and crosslinker and allowed to incubate for 1 h, after which the substrate was rinsed with PBS. To determine the amount of antibody immobilized, $^{125}$I-labelled antibody was used. The amount of surface bound protein was determined using a scintillation counter.

Binding of Radiolabeled Antigen by Immobilized Antibody

The unlabelled antibody-coated substrate was placed in PBS solution of the radiolabeled antigen containing 2 mq/ml BSA for 1 h. It was then washed under rapidly flowing water. The binding of antigen by immobilized antibody was measured using a scintillation counter. Binding of radiolabeled goat IqG (antigen) to surfaces coated with affinity purified rabbit anti-goat IqG, (specific antibody) was designated as "total binding". Binding of labelled antigen to surfaces coated with goat IgG, mouse IqG, or sheep anti-mouse IqG (control antibodies) was designated as "nonspecific adsorption". The percent specific binding was calculated as 100 ×[("total binding" "nonspecific adsorption")/"total binding"].

FIG. 1 summarizes the reaction in the immobilization procedure. Two silane films with thiol terminal groups were evaluated in this study. The thiol group on the silane reacts specifically and covalently with the maleimide region of the heterobifunctional crosslinker GMBS in organic solvent, leaving the succinimide residue of the GMBS available for protein attachment. The time course of GMBS reaction with MDS suggested that 1 h was optimum. The succinimide residue then binds a terminal amino group of the antibody in an aqueous solution through the formation of a stable amide bond.

To prepare a reactive surface silane; films were evaluated as summarized in Table 1. Contact angles of the films were used as a semi quantitative guide to determine film quality and reproducibility. The thiol-terminal films, MDS and MTS exhibited contact angles with the lowest standard deviations for water drops (±3°).

In order to make certain that the reactive groups of the GMBS did not decompose or hydrolyze in either the organic solvent used in attaching it to the silane or in the PBS used in binding it to the protein, the stability of the maleimide and succinimide residues was examined both in organic solvent and in PBS. First, the $^1$H NMR spectrum of GMBS was recorded in anhydrous CDCl$_3$ solution: 2.04 (t,2CH$_2$,-CH$_2$-CH$_2$) 2.66 (t, 2H, N-O-(C=0)-CH$_2$), 2.83 (s, 4H,

TABLE I
EVALUATION OF SILANE FILMS

| Silane Film | Reactive Group | Contact Angle |
|---|---|---|
| ADS | —NH$_2$ | 68 ± 4 |
| ATS | —NH$_2$ | 60 ± 28 |
| MDS | —SH | 54 ± 2 |
| MTS | —SH | 58 ± 3 |
| GTS | —CH——CH$_2$ \ / O | 52 ± 9 |

The reported contact angle is the mean value measured for water drops at various locations on the film-covered surface of three or more cover slips.

TABLE II
EVALUATION OF HETERO-BIFUNCTIONAL CROSSLINKERS

| Hetero-bifunctional Crosslinker | Nonspecific Antigen Adsorption | Total Antigen Binding | Percent Specific Antigen Binding |
|---|---|---|---|
| GMBS | 11 ± 3 ng | 328 ± 17 ng (0.34 ng/mm$^2$) | 97 |
| SPDP | 11 ± 2 ng | 345 ± 70 ng (0.36 ng/mm$^2$) | 97 |
| SIAB | 17 ± 4 ng | 373 ± 63 ng (0.39 ng/mm$^2$) | 95 |
| SMPB | 18 ± 2 ng | 369 ± 109 ng (0.38 ng/mm$^2$) | 95 |

Percent specific antigen binding is calculated by 100 × [(total antigen binding-nonspecific antigen adsorption)/total antigen binding]; total antigen binding represents the amount of labelled antigen (goat IgG) bound to the MDS-coated substrate treated with the specific antibody (rabbid anti-goat IgG) and nonspecific antigen adsorption represents the amount of antigen bound to the MDS-coated substrate treated with control antibody (goat IgG). These experiments were performed in the presence of 2 mg/ml BSA to reduce nonspecific adsorption.

TABLE III
COMPARISON OF ANTIBODY BINDING TO COVER SLIP AND FIBER

| | Cover slip | Optical fiber |
|---|---|---|
| Area | 968 mm$^2$ | 74 mm$^2$ |
| Antibody immobilized | 638 ± 134 ng (0.66 ng/mm$^2$) | 71 ± 3 ng (0.96 ng/mm$^2$) |
| Specific antigen | 350 ± 50 ng | 27 ± 4 ng |

TABLE III-continued

COMPARISON OF ANTIBODY BINDING TO COVER SLIP AND FIBER

| | Cover slip | Optical fiber |
|---|---|---|
| binding | (0.36 ng/mm$^2$) | (0.36 ng/mm$^2$) |

Mean ± S.D. values for antibodies immobilized (rabbit anti-goat IgG, goat IgG, and mouse IgG) and specific antigen binding were calculated from 5 experiments using the MDS film and GMBS crosslinker performed on different days.

N-(C=O)-CH$_2$-CH$_2$), 3.65 (t,2H, N CH$_2$), 6.72 (s,2H,CH=CH). No shift in the assigned peaks was observed after 20, 40, or 60 minutes. Next GMBS was dissolved in minimum amount of DMF and diluted with 1 ml PBS pH 7.4. After 60 min, the mixture was extracted with chloroform. The organic extract was dried and redissolved in CDCl$_3$ The NMR spectrum of the extract in CDCl$_3$ displayed the peaks listed above including resonances for intact succinimide and maleimide groups. These results confirm that GMBS is stable under the conditions employed in the assay system for a period adequate for both the coupling of the crosslinker to the film and the attachment of the protein to the crosslinker.

The amount of antibody coupled to substrates with different geometries was measured by placing radiolabeled antibody on cover slops or fibers coated with MDS and GMBS. The maximum amount of antibody specifically bound to the cover slips was determined to be 0.66 ng/mm$^2$ (4 fmol/mm$^2$) and that on fibers was found to be 0.96 nq/mm$^2$ (6fmol/mm$^2$) (Table III). To establish that the antibody function was maintained during the process, the attachment procedure was repeated with the unlabelled antibody, rabbit anti-goat IgG. The immobilized antibody was then incubated with excess iodinated antigen, goat IqG 0.05 mq/ml. Antigen was bound at the level of 0.36±0.05 ng/mm$^2$ on both cover slips and the fibers (Table III). This level is equivalent to 0.37 to 0.55 moles of antigen bound per mole of immobilized antibody.

Figure 2:
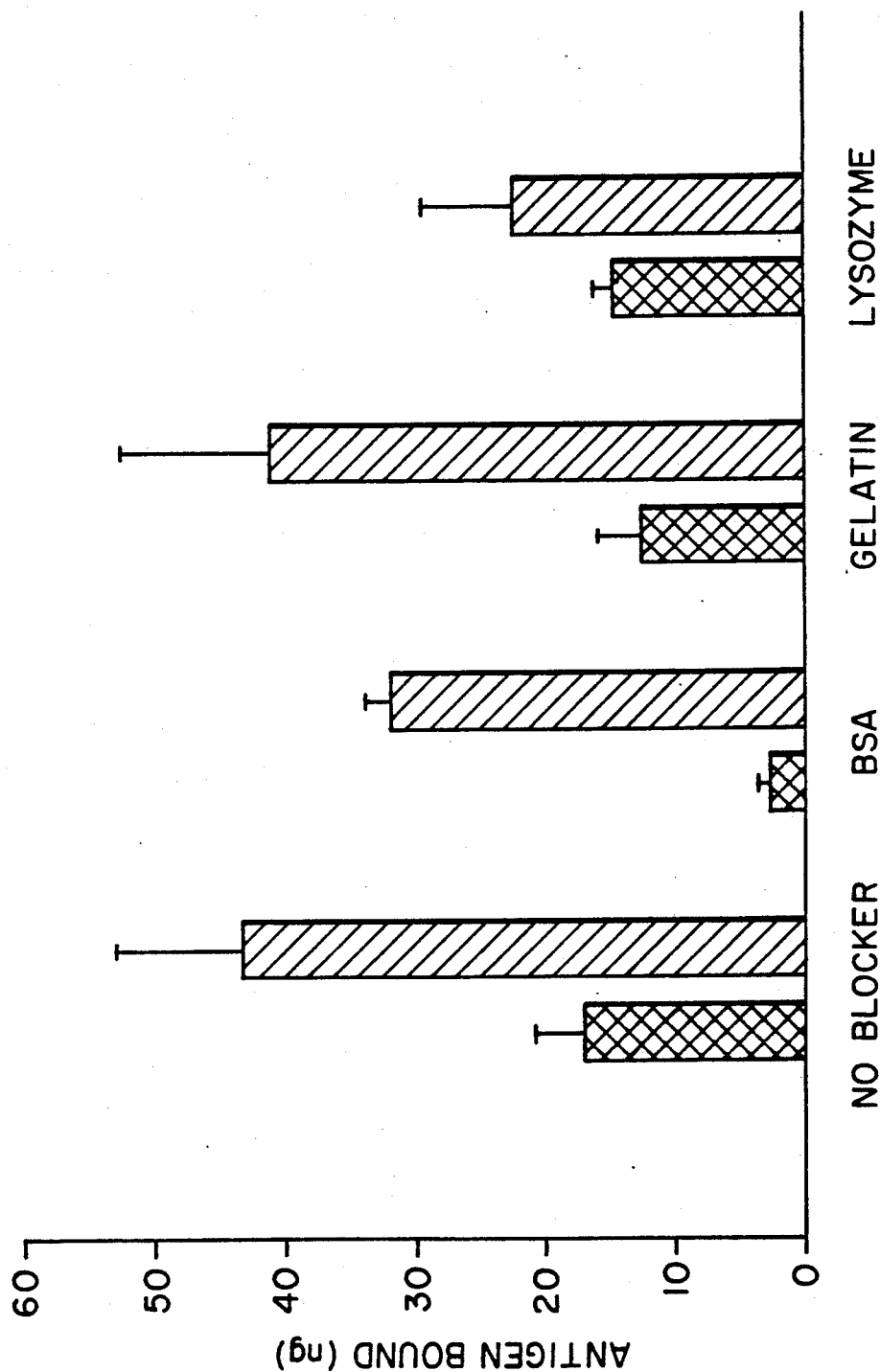
FIG. 2 is a graphic illustration of the effect of various blockers on the nonspecific protein adsorption. Optical fibers coated with goat IqG XX (control antibody) or rabbit anti goat IqG (specific antibody //) were incubated with blocking agent (0.05 mg/ml) for one hour followed by incubation with 0.05 mg/ml iodinated antigen (goat IgG) for one hour. The fibers were then washed and radioactivity measured.

A problem initially encountered in using the antibody-coated silica substrate was nonspecific adsorption of the antigen. Several commonly used blocking agents, e.g. BSA, gelatin, lysozyme, Triton X 100, (a detergent) and Tween 20, (a detergent) were tested with this system to determine their effect on nonspecific antigen adsorption. Each of the blocking agents in FIG. 2 were dissolved in PBS to a final concentration of 0.05 mg/ml. The silica coated with either specific antibody (affinity purified rabbit anti goat IqG) or control antibody (goat IgG) was then incubated with the blocking agent for 1 h, washed with PBS, and then immersed in the labelled goat IgG (antigen) solution. It was found that BSA was the most effective in blocking the nonspecific adsorption of proteins to a surface modified with MDS, GMBS and control antibody. 2 mg/ml was found to be the optimum BSA concentration. When BSA (2 mq/ml) was used as the blocking agent, the levels of nonspecific adsorption were significantly reduced: nonspecific adsorption represented 2-6% of the total binding for antigen concentration ≦0/1 mq/ml. In order to simplify the procedure and reduce the incubation time for the entire process, subsequent experiments were performed in which BSA and the antigen were combined in the same solution. The results obtained using this method were equivalent to those obtained by adding the blocking agent and antigen separately.

The versatility of the antibody immobilization procedure was tested with different crosslinkers and shown in Table II. Four heterobifunctional crosslinkers with amine reactive succinimide groups were used differing from each other by their thiol reactive sites, which were maleimidyl (GMBS), pyridyldithio (SPDP), iodoacetyl (SIAB) and maleimidiphenyl (SMPB). Antibody immobilized using each of the four crosslinkers bound the same amount of antigen in the presence of 2 mq/ml BSA.

Since, in the previously described experiments, goat IgG was used as both control antibody and as the antigen, other sources of IqG were also tested as control antibodies. Iodinated goat IgG antigen (0.05 mq/ml) in 2 mq/ml BSA was incubated for 1 h. with cover slips coated with equivalent amounts of goat IqG, mouse IqG, or sheep anti mouse IgG (control antibodies) or rabbit anti goat IqG (specific antibody). Nonspecific adsorption of antigen to cover slips coated with the antibodies was 1.9±0.2%, 2.1±0.2%, 3.1±0.2% respectively, of levels of total antigen bound to cover slips coated with the specific antibody. Since there was no significant variation in nonspecific adsorption, goat IgG was used as the "control antibody" in the remaining experiments.

To determine the applicability of antibody-coated silica surfaces for the binding of antigen, an immunoassay was performed. Antibody coated cover slips were incubated for 1 h with varying concentrations of radiolabeled antigen (0.5 uq/ml to 750 ng) and BSA (2 mq/ml) in PBS (FIG. 3). The substrate coated with control antibody was also incubated with iodinated antigen and binding values were used to determine nonspecific antigen adsorption. These experiments show that as little as 24 nq (150 fmoles) of bound antigen can be detected on a glass cover slip immersed in a 0.5 uq/ml (3pmoles/ml) antigen solution. Nonspecific antigen adsorption was less than 5% of total antigen binding for antigen solutions ranging from 0.5-100 uq/ml (3-625 pmoles/ml). Amounts of antigen bound increased exponentially over this range.

The advantages of the present invention are evident not only in terms of simplicity and reproducibility of immobilization as with antibodies, but also, in terms of subsequent antigen binding capacity in the range of antigen concentrations measurable. When thiol terminal silanes and heterobifunctional crosslinkers are used, the problem of inter protein crosslinking can be avoided. The amount of antigen bound by immobilized antibody can be directly proportional to the concentration of applied antigen over approximately three orders of magnitude as shown in FIG. 3. Furthermore, antigen binding can be measured on coverslips or fibers exposed to antigen concentrations as low as 0.5 micrograms/ml (3 pmol/ml).

In another example of this invention the enzyme acetylcholine esterase is immobilized on a metal (Pt) surface. Platinum foil is cut into small strips of 1×3 cm. The metal surface is either flame cleaned or plasma etched to get a reactive oxidized surface. The metal strip is then treated with a 2% solution of either MDS or MTS in dry toluene under nitrogen atmosphere for 2 h. It is removed from the silane solution, washed with toluene and air dried. Next, the silanized metal surface is reacted with a solution (2mM) of heterobifunctional crosslinking reagent (e.g. GMBS) in dimethylformamide (DMF) and absolute ethanol. After 1 h, the platinum is take out and washed with A 0.05 mg/ml solution off $^{125}$-I labelled enzyme (acetylcholinesterase) is incubated with the above sample for a period of 1 h. The sample is washed in a rapid flow of water and the amount of bound enzyme is calculated using a scintillation counter. The activity of the immobilized enzyme is measured by placing the sample in a solution of enzyme-substrate (acetylcholine) hydrolysable by enzyme, containing an indicator (e.g. bromothymol blue) and observing color change due to pH variation. Alternatively pH changes can also be determined amperometricly or potentiometricly with the platinum as an electrode. The enzyme is bound to the metal and is found to maintain its ability to carry out catalytic action.

In still another example of this invention nucleic acid probes are immobilized on solid surfaces. Nucleic acid probes with a desired sequence of bases is synthesized using a commercially available synthesizer. The synthesis is manipulated in such a way that the first or last base (either purine or pyrimidine) in the sequence would have an additional amino group. Two such commercially available bases that are used include 2,6 diaminipurine and 2,4-diamino 6-hydroxypyrimidine.

A solid substrate (either silica or platinum) is silanized with a thiol-terminal silane and to it a heterobifunctional crosslinker attached as we have shown in the above examples (i.e. MTS and GMBS). The probe is duplexed with a complementary strand of nucleic acids to protect the amino groups that are not on the end. After addition of the duplex to the modified surface, the amino groups on bases at the end would specifically bind to amine reactive succinimide residue of the crosslinker without significantly disturbing the configuration of other bases. After the reaction of the end base and the succinimide is complete ($\leq 1$ hr), the duplex is melted, removing the unimmobilized, complementary nucleic acid chain. The result is a single chain nucleic acid probe immobilized through a crosslinker to a silane film on a solid substrate.

The above illustrative examples are not meant to be in anyway limiting of the invention. Various times, temperatures and other variables can be used in all of the reactions noted consistent with obtaining a bound protein or other active agent at high concentrations on the surface. The thiol terminal silane film used in the specific examples are particularly attractive because they allow protein to be immobilized without chemical modification; thus, adding to convenience, efficiency and lowering the time and complexity of processes in accordance with the present invention. While succinimide terminal crosslinkers have been specifically described in the examples, other bifunctional crosslinkers can be used. Similarly a variety of combinations of substrates, heterobifunctinal crosslinkers, silanes and active agents can be used.

We claim:

1. A method for modifying a substrate to activate said substrate for the immobilization of anzime group-containing active agents, said method comprising,
    selecting a substrate having hydroxyl groups on at least one surface,
    coating said hydroxyl-containing surface with a thiol-terminal group silane containing a reactive group other than a thiol group that reacts only with the hydroxyl groups on said surface to form a silane layer having an available reactive thiol group,
    coating said silane layer with a heterobifunctional succinimide group-containing crosslinking agent having a functional group other than the succinimide group that reacts only with the thiol-terminal group on said silane to form a layer of crosslinking agent having an available free succinimide reactive group capable of reacting with amino group of said active agent.

2. A method in accordance with the method of claim 1 and further comprising, coating said layer of crosslinking agent with an active agent having an amine group that reacts with the available reactive succinimide group on the crosslinking agent.

3. A method in accordance with claim 1 wherein said silane is mercaptomethyldimethylethoxysilane.

4. A method in accordance with claim 1 wherein said silane is mercaptopropyltrimethoxysilane.

5. A method in accordance with the method of claim 1 wherein said heterobifunctional crosslinking agent is N gamma-maleimidobutyryloxy succinimide ester.

6. A method in accordance with the method of claim 1 wherein said heterobifunctional crosslinking agent is N-succinimidyl-3 (2-pyridyldithio) propionate.

7. A method in accordance with the method of claim 1 wherein said heterobifunctional crosslinking agent is N-succinimdyl (4-iodoacetyl) aminobenzoate.

8. A method in accordance with the method of claim 1 wherein said heterobifunctional crosslinking agent is succinimidyl 4-(p-maleimidophenyl) butyrate.

9. A method in accordance with claim 1 wherein said substrate is formed of an inorganic material.

10. A method in accordance with claim 1 wherein said succinimide group is on one end of said crosslinking agent.

11. A product for supporting an active agent amino group-containing produced by the method of claim 1.

12. A product in accordance with claim 11 and further comprising,
    a layer of amino group-containing active agent bound by said amino group to the free succinimide reactive group of said crosslinking agent.

13. The product of claim 11 wherein said substrate is an inorganic substrate.

14. The product of claim 11 wherein said silane is mercaptomethyldimethylethoxysilane.

15. The product of claim 11 wherein said silane is mercaptopropyltrimethoxysilane.

16. The product of claim 11 wherein said crosslinking agent is N-gamma-maleimidobutyryloxy succinimide ester.

17. The product of claim 11 wherein said crosslinking agent is N succinimidyl-3 (2-pyridyldithio) propionate.

18. The product of claim 11 wherein said crosslinking agent is N-Succinimdyl-(4-iodoacetyl)aminobenzoate.

19. The product of claim 11 wherein said crosslinking agent is succinimidyl 4-(p-maleimidophenyl) butyrate.

20. The product of claim 12 wherein said crosslinking agent is succinimidyl 4 (maleimidophenyl) butyrate.

21. A product of claim 11 wherein said succinimide group is on one end of said crosslinking agent.

22. In a method of immobilizing an amino group-containing active agent on a substrate, the improvement comprising preparing said substrate by,
    selecting a substrate having hydroxyl groups on a surface thereof,
    depositing on the substrate of film of a thiol-terminal group silane having a reactive group other than the thiol group that reacts with said hydroxyl groups to form silane surface having a free reactive thiol group, coating said silane surface with a heterobifunctional succinimide group-containing crosslinking agent having a functional group other than the succinimide group that reacts with said free reactive thiol group to form a layer of the crosslinking agent having an available free succinimide reactive group that reacts with the amino group of said active agent.

23. A method in accordance with the method of claim 22 wherein said active agent is selected from the group consisting of enzymes, nucleic acid probes, lectins, chelators, ionophores, lipids, and biological cells.

24. A method in accordance with claim 23 herein said substrate is inorganic.

25. A method in accordance with the method of claim 22 wherein said active agent is selected from the group consisting of antibodies and antigens.

26. A method in accordance with the method of claim 22 wherein said active agent is a protein.

27. A method in accordance with the method of claim 22 wherein said active agent is a receptor.

* * * * *

UNITED STATES PATENT AND TRADEMARK OFFICE
CERTIFICATE OF CORRECTION

PATENT NO. : 5,077,210
DATED : December 31, 1991
INVENTOR(S) : Eigler et al.

It is certified that error appears in the above-identified patent and that said Letters Patent is hereby corrected as shown below:

<u>Title page,</u>
Items [19] and [76], please delete the inventor's name: Frances S. Eigler and insert therefor: -- Frances S. Ligler --

Signed and Sealed this

Eighth Day of January, 2002

*Attest:*

JAMES E. ROGAN
*Attesting Officer*     *Director of the United States Patent and Trademark Office*